(12) United States Patent
Slinkard et al.

(10) Patent No.: US 8,410,461 B2
(45) Date of Patent: Apr. 2, 2013

(54) METHODS AND APPAREL FOR ATTENUATING ELECTROMAGNETIC FIELDS EMANATING FROM A PERSON IN A HUMAN ADVERSARIAL SITUATION

(76) Inventors: Michael D. Slinkard, John Day, OR (US); John M. Maupin, John Day, OR (US); Scott J. Eastman, Reno, NV (US)

( * ) Notice: Subject to any disclaimer, the term of this patent is extended or adjusted under 35 U.S.C. 154(b) by 0 days.

(21) Appl. No.: 13/279,307

(22) Filed: Oct. 23, 2011
(Under 37 CFR 1.47)

(65) Prior Publication Data
US 2012/0273699 A1 Nov. 1, 2012

Related U.S. Application Data

(63) Continuation of application No. PCT/US2010/032133, filed on Apr. 22, 2010.

(51) Int. Cl.
*G21F 3/02* (2006.01)
(52) U.S. Cl. ............... 250/519.1; 250/505.1; 250/515.1; 250/516.1; 2/69
(58) Field of Classification Search .................. None
See application file for complete search history.

(56) References Cited

U.S. PATENT DOCUMENTS

| | | | |
|---|---|---|---|
| 3,380,087 A | 4/1968 | Petty et al. | |
| 3,822,403 A | 7/1974 | Coleman et al. | |
| 4,211,980 A | 7/1980 | Stowell | |
| 4,495,239 A * | 1/1985 | Pusch et al. | 428/192 |
| 4,621,012 A * | 11/1986 | Pusch | 442/228 |
| 4,640,851 A * | 2/1987 | Pusch | 428/17 |
| 4,653,473 A | 3/1987 | Kempe | |
| 4,743,478 A * | 5/1988 | Pusch | 428/17 |
| 4,825,877 A | 5/1989 | Kempe | |
| 4,868,580 A | 9/1989 | Wade | |
| 4,926,910 A | 5/1990 | Wade | |
| 5,077,101 A * | 12/1991 | Conway et al. | 428/17 |
| 5,097,885 A | 3/1992 | Kitagawa | |
| 5,103,504 A | 4/1992 | Dordevic | |
| 5,203,033 A | 4/1993 | Sheppard et al. | |
| D337,366 S | 7/1993 | Baker | |

(Continued)

FOREIGN PATENT DOCUMENTS

| | | |
|---|---|---|
| DE | 3217977 | 11/1983 |
| DE | 3217977 A1 * | 11/1983 |

(Continued)

OTHER PUBLICATIONS

Loscher et al; Conspicuous behavioral abnormalities in a dairy cow herd near a TV and Radio transmitting antenna; Practical Veterinary Surgeon vol. 79 No. 5 p. 437 (1998).

(Continued)

*Primary Examiner* — Andrew Smyth
(74) *Attorney, Agent, or Firm* — David S. Alavi

(57) ABSTRACT

A method comprises attenuating, while involved in a human adversarial situation, one's own emanated electromagnetic field at frequencies less than about 1 gigahertz by wearing one or more articles of apparel that include an electromagnetically shielding fabric. Another method comprises (i) providing to the user the one or more articles of apparel that include an electromagnetically shielding fabric, and (ii) instructing the user to wear at least one of the articles of apparel while involved in the human adversarial situation. The shielding fabric comprises a substantially continuous system of conductive fibers combined with a non-conductive fabric and attenuates the emanated electromagnetic field at frequencies less than about 1 gigahertz. Attenuating the emanated electromagnetic field at frequencies less than about 1 gigahertz decreases the likelihood of that emanated field affecting progress or an outcome of the human adversarial situation.

25 Claims, 6 Drawing Sheets

U.S. PATENT DOCUMENTS

| | | | |
|---|---|---|---|
| 5,312,678 A * | 5/1994 | McCullough et al. | 442/189 |
| D350,399 S | 9/1994 | Bodrie | |
| 5,348,789 A * | 9/1994 | Hellwig | 428/135 |
| 5,377,711 A | 1/1995 | Mueller | |
| 5,521,655 A | 5/1996 | Rhoad | |
| 5,573,857 A | 11/1996 | Auger | |
| 5,578,359 A * | 11/1996 | Forbes et al. | 428/131 |
| 5,621,188 A | 4/1997 | Lee et al. | |
| 5,675,838 A | 10/1997 | Hollinger | |
| 5,676,812 A | 10/1997 | Kadokura | |
| 5,767,933 A | 6/1998 | Hagan | |
| 5,935,706 A | 8/1999 | Hoover et al. | |
| 5,968,854 A | 10/1999 | Akopian et al. | |
| 5,983,913 A | 11/1999 | Fargason | |
| 6,061,828 A | 5/2000 | Josephs | |
| 6,127,022 A * | 10/2000 | Pretorius | 428/195.1 |
| 6,134,718 A | 10/2000 | Sesselmann | |
| 6,146,351 A | 11/2000 | Kempe | |
| 6,265,466 B1 | 7/2001 | Glatkowski et al. | |
| 6,269,489 B1 | 8/2001 | Heath | |
| 6,299,812 B1 | 10/2001 | Newman | |
| 6,539,966 B2 | 4/2003 | Raines et al. | |
| 6,632,499 B1 | 10/2003 | Marks et al. | |
| 6,694,995 B1 | 2/2004 | Ransom | |
| 6,868,854 B2 | 3/2005 | Kempe | |
| 6,941,961 B1 | 9/2005 | Eastman | |
| 7,100,626 B2 | 9/2006 | Livacich | |
| 7,134,857 B2 | 11/2006 | Andrady | |
| 7,182,091 B2 | 2/2007 | Maddox | |
| 7,196,023 B2 | 3/2007 | Langley et al. | |
| 7,208,115 B2 | 4/2007 | Sheridan et al. | |
| 7,354,877 B2 | 4/2008 | Rosenberger et al. | |
| 7,565,909 B2 | 7/2009 | Reis et al. | |
| 8,188,452 B2 | 5/2012 | Slinkard et al. | |
| 8,203,129 B2 | 6/2012 | Slinkard et al. | |
| 8,212,229 B2 | 7/2012 | Slinkard et al. | |
| 2001/0000849 A1 | 5/2001 | Siman-Tov et al. | |
| 2001/0022189 A1* | 9/2001 | Hexels | 135/121 |
| 2002/0069449 A1 | 6/2002 | Blutstein et al. | |
| 2002/0069904 A1 | 6/2002 | Robinson | |
| 2003/0233694 A1 | 12/2003 | Wescombe-Down | |
| 2004/0053780 A1 | 3/2004 | Jiang et al. | |
| 2004/0068415 A1 | 4/2004 | Soloman | |
| 2004/0107474 A1* | 6/2004 | Sesselmann | 2/69 |
| 2004/0188890 A1* | 9/2004 | Sheridan et al. | 264/510 |
| 2004/0207566 A1 | 10/2004 | Essig et al. | |
| 2004/0209051 A1 | 10/2004 | Santos et al. | |
| 2006/0033674 A1 | 2/2006 | Essig et al. | |
| 2006/0094315 A1 | 5/2006 | Brodsky | |
| 2006/0147698 A1 | 7/2006 | Carroll et al. | |
| 2006/0170221 A1 | 8/2006 | Wobben | |
| 2006/0264137 A1 | 11/2006 | Gunje et al. | |
| 2007/0226868 A1 | 10/2007 | Hunt | |
| 2008/0210175 A1* | 9/2008 | Bryce | 119/720 |
| 2009/0036012 A1 | 2/2009 | Nhan et al. | |
| 2009/0184269 A1 | 7/2009 | Rees | |
| 2009/0317596 A1* | 12/2009 | Flavin | 428/172 |
| 2011/0079257 A1 | 4/2011 | Slinkard et al. | |
| 2011/0095931 A1* | 4/2011 | Child | 342/3 |
| 2011/0192354 A1 | 8/2011 | Slinkard et al. | |

FOREIGN PATENT DOCUMENTS

| | | |
|---|---|---|
| EP | 1 096 604 | 5/2001 |
| EP | 1096604 A1 * | 5/2001 |
| JP | 10-046443 | 2/1998 |
| JP | 10046443 A * | 2/1998 |
| JP | 2002-054055 | 2/2002 |
| KR | 10-1994-0010630 | 10/1994 |
| KR | 10-2000-0007920 | 2/2000 |
| KR | 10-2003-0061535 | 7/2003 |
| KR | 10-0433389 | 5/2004 |
| KR | 20-0416156 | 5/2006 |
| WO | WO 90/09473 | 8/1990 |
| WO | WO 97/48964 | 12/1997 |
| WO | WO 2010/124145 | 10/2010 |

OTHER PUBLICATIONS

Trzeciak et al; Behavioral effects of long-term exposure to magnetic fields in rats; Bioelectromagnetics vol. 14 No. 4 p. 297 (1993).

Pyrek, Kelly M.; Antimocrobials: Healthcare's Silver Bullet Against HAIs?; www.infenctioncontroltoday.com; online article posted Aug. 28, 2008.

International Search Report and Written Opinion of the International Searching Authority in co-owned App No. PCT/US2010/032133, (2010).

Office Action dated Apr. 13, 2011 in co-owned U.S. Appl. No. 12/347,967.

Office Action dated Jan. 5, 2012 in co-owned U.S. Appl. No. 12/347,967.

Notice of Allowance dated Apr. 23, 2012 in co-owned U.S. Appl. No. 12/347,967.

Office action dated Dec. 10, 2010 in co-owned U.S. Appl. No. 12/428,763.

Office Action dated Jun. 21, 2011 in co-owned U.S. Appl. No. 12/428,763.

Notice of Allowance dated May 21, 2012 in co-owned U.S. Appl. No. 12/428,763.

Office Action dated Sep. 3, 2010 in co-owned U.S. Appl. No. 12/347,971.

Office Action dated Feb. 7, 2011 in co-owned U.S. Appl. No. 12/347,971.

Notice of Allowance dated Jun. 15, 2011 in co-owned U.S. Appl. No. 12/347,971.

Office Action dated Oct. 14, 2011 in co-owned U.S. Appl. No. 12/347,971.

Office Action dated Aug. 13, 2012 in co-owned U.S. Appl. No. 12/347,971.

Office Action dated Apr. 18, 2011 in co-owned U.S. Appl. No. 12/549,698.

Office Action dated Jan. 6, 2012 in co-owned U.S. Appl. No. 12/549,698.

Notice of Allowance dated May 7, 2012 in co-owned U.S. Appl. No. 12/549,698.

Office Action dated Jul. 14, 2011 in co-owned U.S. Appl. No. 12/701,169.

Office Action dated Apr. 13, 2012 in co-owned U.S. Appl. No. 12/701,169.

* cited by examiner

METHODS AND APPAREL FOR ATTENUATING ELECTROMAGNETIC FIELDS EMANATING FROM A PERSON IN A HUMAN ADVERSARIAL SITUATION

BENEFIT CLAIMS TO RELATED APPLICATIONS

This application is a continuation of: (i) international App. No. PCT/US2010/032133 filed Apr. 22, 2010 in the names of Michael D. Slinkard, John M. Maupin, and Scott J. Eastman and entitled "Methods and apparel for attenuating electromagnetic fields emanating from a person," and (ii) US non-provisional application Ser. No. 12/701,169 filed Feb. 5, 2010 in the names of Michael D. Slinkard, John M. Maupin, and Scott J. Eastman and entitled "Methods and apparel for simultaneously attenuating electromagnetic fields and odors emanating from a person"; each of said applications is hereby incorporated by reference as if fully set forth herein.

BACKGROUND

The field of the present invention relates to methods and apparel for attenuating electromagnetic fields emanating from a person while that person is in a human adversarial situation.

In addition to those applications listed above, the subject matter disclosed or claimed herein may be related to subject matter disclosed or claimed in: (i) U.S. non-provisional application Ser. No. 12/549,698 filed Aug. 28, 2009 in the names of Michael D. Slinkard and John M. Maupin and entitled "Methods and apparel for attenuating electromagnetic fields emanating from a person in or on a body of water," (ii) U.S. non-provisional application Ser. No. 12/428,763 filed Apr. 23, 2009 in the names of Michael D. Slinkard and John M. Maupin and entitled "Methods and apparel for attenuating electromagnetic fields emanating from an animal handler," (iii) U.S. non-provisional application Ser. No. 12/347,971 filed Dec. 31, 2008 in the names of Michael D. Slinkard and John M. Maupin and entitled "Methods and hunting blind for attenuating electromagnetic fields emanating from a hunter," and (iv) U.S. non-provisional application Ser. No. 12/347,967 filed Dec. 31, 2008 in the names of Michael D. Slinkard and John M. Maupin and entitled "Methods and apparel for attenuating electromagnetic fields emanating from a hunter"; each of said applications is incorporated by reference as if fully set forth herein.

It is known that the human body generates electromagnetic fields during normal body functions, and that those fields can increase in strength with increased activity, excitement, emotion, or attention. For example, brain activity, nerve activity, and muscle activity all result in electric fields that emanate from the body. Detection and characterization of such fields form the basis for the conventional clinical techniques of electrocardiography (i.e., ECG or EKG), electroencephalography (i.e., EEG), and electromyelography (i.e., EMG). For the purposes of the present disclosure or claims, "electromagnetic" is intended to denote those fields that have temporal variations well below so-called optical frequencies (i.e., having frequency components no greater than about 1 gigahertz (GHz), typically no greater than about 1 megahertz (MHz), and often no greater than about 1 kilohertz (kHz).

It is also known that at least some animals can detect or respond to electromagnetic fields. For example, sharks detect electric fields emanating from prey by means of special sensing organs called the ampullae of Lorenzini (http://en.wikipedia.org/wiki/Ampullae_of_Lorenzini). A shark-repelling system is disclosed in U.S. Pat. No. 4,211,980 that generates an electric field to drive away the sharks. Other animals are believed to navigate their natural migratory routes using the earth's magnetic field (http://www.pbs.org/wgbh/nova/magnetic/animals.html).

Fabrics exist that are adapted to attenuate or block electromagnetic fields. They typically include electrically conductive fibers (e.g., metal, carbon nanotubes, or other conductive fibers) incorporated into the fabric along with more typical textile fibers. Garments constructed from such fabrics are conventionally used to shield a human wearer from surrounding electromagnetic fields. Such shielding can be usefully employed into safety equipment or apparel, can be worn by or applied to a patient to provide various health or therapeutic benefits, or for other purposes. Examples of such fabrics and their uses can be found in the following references, each of which is incorporated by reference as if fully set forth herein:

U.S. Pat. No. 7,354,877 entitled "Carbon nanotube fabrics" issued Apr. 8, 2008 to Rosenberger et al;

U.S. Pat. No. 6,868,854 entitled "Method and article for treatment of fibromyalgia" issued Mar. 22, 2005 to Kempe;

Pat. Pub. No. 2004/0053780 entitled "Method for fabricating nanotube yarn" published Mar. 18, 2004 in the names of Jiang et al;

U.S. Pat. No. 6,265,466 entitled "Electromagnetic shielding composite comprising nanotubes" issued Jul. 24, 2001 to Glatkowski et al;

U.S. Pat. No. 6,146,351 entitled "Method of reducing delayed onset muscle soreness" issued Nov. 14, 2000 to Kempe;

U.S. Pat. No. 5,621,188 entitled "Air permeable electromagnetic shielding medium" issued Apr. 15, 1997 to Lee et al;

U.S. Pat. No. 4,825,877 entitled "Method of pain reduction using radiation-shielding textiles" issued May 2, 1989 to Kempe; and U.S. Pat. No. 4,653,473 entitled "Method and article for pain reduction using radiation-shielding textile" issued Mar. 31, 1987 to Kempe.

There is no teaching or suggestion in the prior art to attenuate or block electromagnetic fields emanating from a human body while involved in a human adversarial situation, or that such attenuation or blocking would be desirable.

SUMMARY

A method comprises attenuating, while involved in a human adversarial situation, one's own emanated electromagnetic field at frequencies less than about 1 gigahertz by wearing one or more articles of apparel that include an electromagnetically shielding fabric. Another method comprises (i) providing to a user the one or more articles of apparel that include an electromagnetically shielding fabric, and (ii) instructing the user to wear at least one of the articles of apparel while involved in the human adversarial situation. The shielding fabric comprises a substantially continuous system of conductive fibers combined with a non-conductive fabric and attenuates the emanated electromagnetic field at frequencies less than about 1 gigahertz. Attenuating of the emanated electromagnetic field at frequencies less than about 1 gigahertz decreases the likelihood of that emanated field affecting progress or an outcome of the human adversarial situation.

Objects and advantages pertaining to apparel incorporating electromagnetic shielding fabric may become apparent upon referring to the exemplary embodiments illustrated in the drawings and disclosed in the following written description or appended claims.

This summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Figure 1A:
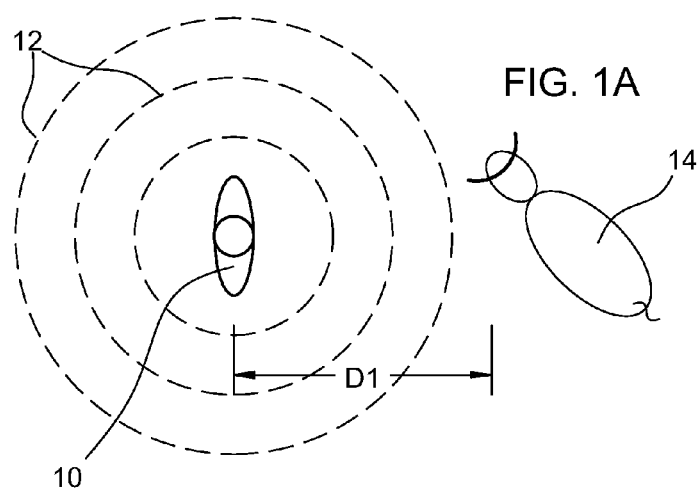
FIGS. 1A and 1B are schematic top views illustrating the approach of a hunter toward a prey animal (or vice versa) with and without, respectively, electromagnetically shielding apparel.

The embodiments shown in the Figures are exemplary, and should not be construed as limiting the scope of the present disclosure or appended claims.

DETAILED DESCRIPTION OF EMBODIMENTS

Attenuating or blocking electromagnetic fields emanating from a person can be advantageous while involved in an adversarial situation, particularly human adversarial situations in which the human adversary is aware of the person's presence. A human adversary can be affected by emotional responses or the emotional state of a person nearby, e.g., a person's anxiety can alert or cue a human adversary, or a person's fear can trigger an aggressive response from the human adversary. Sensing by a human adversary of a person's emotional state or response might occur in a variety of ways, e.g., by detecting by smell sweat or pheromones released as a result of the person's emotional state or response, or by sensing emotion-related electromagnetic fields resulting from the person's emotional state or responses. Attenuating or blocking electromagnetic fields emanating from the person can advantageously reduce any alerting or cueing of a human adversary arising from an emotional state or an emotional response of the person, and thereby reduce any advantage that might have been gained from that alerting or cueing.

An "adversarial situation" shall include any situation in which a person involved vies with a human adversary. The nature of such situations can vary widely, and can include, inter alia: (i) a team or individual athletic contest of any sort (particularly those requiring a high degree of mental concentration); (ii) a mental or verbal contest of any sort (e.g., a debate); (iii) board or card games of any sort; (iv) an interview, debriefing, or interrogation (either participant); (v) law enforcement situations; (vi) military, combat, or tactical situations; (vii) covert operations; or (viii) other adversarial situations involving interaction between a person and a human adversary, particularly those situations in which the human adversary is aware of the person's presence.

An exemplary method comprises attenuating, while a person is in an adversarial situation, the electromagnetic field emanated by the person at frequencies less than about gigahertz. The electromagnetic field are attenuated by one or more articles of electromagnetically shielding apparel worn by the person while involved in the adversarial situation. The article of electromagnetically shielding apparel comprises an electromagnetically shielding fabric. The fabric comprises a substantially continuous system of conductive fibers combined with a non-conductive fabric and attenuates electromagnetic fields at frequencies less than about 1 gigahertz. Another exemplary method can include providing one or more articles of electromagnetically shielding apparel to a person and instructing that person to wear at least one of the articles of electromagnetically shielding apparel while involved in an adversarial situation. That method can also include constructing at least one of the articles of electromagnetically shielding apparel prior to providing it to the person. There is no teaching or suggestion in the prior art to attenuate or block electromagnetic fields at frequencies less than about 1 gigahertz emanating from a person while involved in an adversarial situation, or that such attenuation or blocking would be desirable.

A person wears the article of electromagnetically shielding apparel while involved in an adversarial situation (e.g., a poker player at the gaming table; a golfer on the course; or a police detective in the interrogation room). Instead or in addition, other people likely to be near the adversarial situation (i.e., spectators or bystanders) can wear articles of electromagnetically shielding apparel; the following description applied to both a person involved in the adversarial situation as well as spectators, bystanders, or other persons nearby (e.g., near enough to affect the persons or adversaries involved in the adversarial situation via emanated electromagnetic fields). By blocking or attenuating electromagnetic fields emanating from a person near a human adversary, the adversary is less likely to sense such fields that arise from an emotional response or state of the person, and is therefore also less likely to react to that emotional state or reaction. In particular, emotional responses or states that might alert or cue the adversary are less likely to be sensed by the adversary. Such emotional states or responses can arise for a variety of reasons, e.g., a person's or bystander's fear of the human adversary, or a person's or bystander's frustration with the adversary's behavior or response (or lack thereof).

Figure 2:
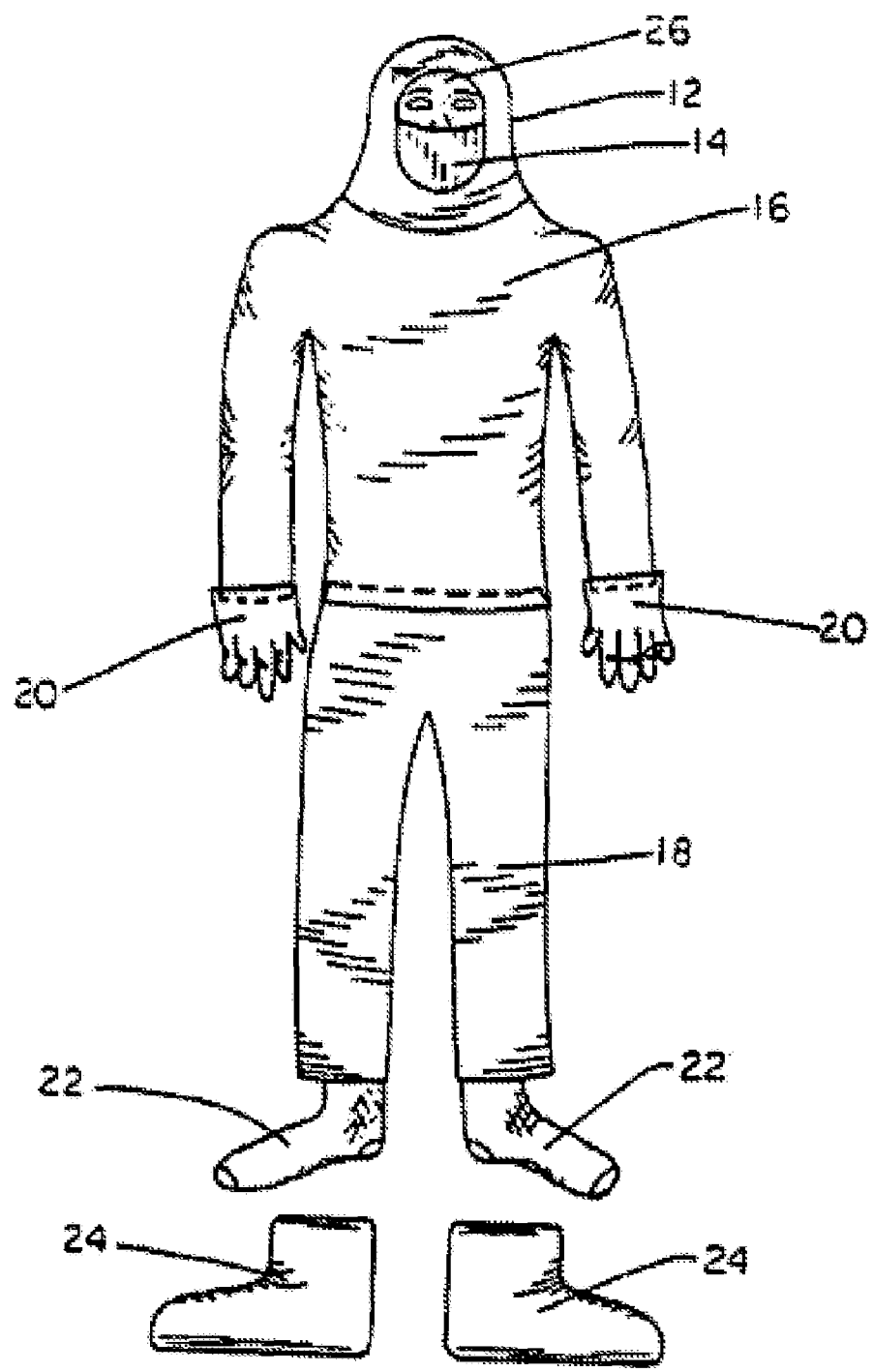
FIG. 2 illustrates various exemplary articles of electromagnetically shielding apparel.

As illustrated by the examples of FIG. 2, an article of apparel incorporating electromagnetically shielding fabric can comprise an article of clothing (e.g., pants 18, shorts, shirt 16, undergarments, leggings, sleeves, gloves 20, mittens, jacket, coat, vest, overalls, waders, or snowsuit), footwear (e.g., shoes, boots 24, socks 22, or boot liners), headwear (e.g., hood 12, facemask 14, or hat), or eyewear (e.g., glasses or goggles 26).

Electromagnetically shielding apparel can be advantageously employed during other activities or in other situations. Attenuating or blocking electromagnetic fields at frequencies less than about 1 gigahertz emanating from a person can also be advantageous while handling an animal. It has been observed frequently that animals can be affected by emotional responses or the emotional state of a person nearby, e.g., a person's anxiety can cause nervous or uneasy behavior of the animal, or a person's fear can trigger an aggressive or attack response from the animal. Sensing by an animal of a person's emotional state or response might occur in a variety of ways, e.g., by detecting by smell pheromones released as a result of the person's emotional state or response, or by sensing emotion-related electromagnetic fields resulting from the person's emotional state or responses. Attenuating or blocking fields emanating from the person can advantageously reduce the effect on the animal of the emotional state or an emotional response of the person. There is no teaching or suggestion in the prior art to attenuate or block electromagnetic fields emanating from an animal handler while handling an animal, or that such attenuation or blocking would be desirable.

An exemplary method comprises attenuating, while handling an animal, the electromagnetic field emanated by a handler of the animal. The electromagnetic field is attenuated by one or more articles of apparel worn by the handler while handling the animal. The articles of apparel comprise an electromagnetically shielding fabric, which fabric comprises a substantially continuous system of conductive fibers combined with a non-conductive fabric. Another exemplary method can include providing one or more such articles of electromagnetically shielding apparel to a handler and instructing that handler to wear the articles while handling the animal. That method can also include constructing at least one of the articles of apparel prior to providing it to the handler.

"Handling" an animal shall encompass, inter alia: (i) literal handling of the animal by holding or touching the animal; (ii) handling the animal using a rope, chain, leash, muzzle, harness, saddle, reins, yoke, prod, whip, or other equipment; (iii) feeding the animal; (iv) guiding, directing, herding, capturing, or restraining the animal; (v) riding the animal; (vi) using the animal to pull or push a vehicle, object, or equipment of any sort; (vii) using the animal in a performance, display, or demonstration; (viii) training the animal for any purpose, including but not limited to those listed here; (ix) conducting veterinary examination or treatment of the animal; (x) using an animal to train another handler to perform any animal-handling task, including but not limited to those listed here; (xi) using an animal to learn from another handler to perform any animal-handling task, including but not limited to those listed here; and (xii) other activities that involve interaction between a person and an animal. Examples of animals that might be "handled" include but are not limited to: dogs, e.g., owned by the handler or by another, stray, domesticated, show, police or other law enforcement, feral, or wild; cats, e.g., domestic, feral, wild, large predators in the wild or in captivity; zoo, circus, or other exhibited animals; horses, oxen, mules, donkeys, burros, llamas, or other pack or utility animals; cows, pigs, goats, sheep, poultry, or other livestock or herd animals.

An animal handler wears the article of electromagnetically shielding apparel while handling the animal. Instead or in addition, other people likely to be near the animal (i.e., bystanders) can wear articles of electromagnetically shielding apparel; for purposes of the present disclosure or appended claims, the terms "handler" and "handling" shall be construed as including both those persons interacting directly with the animal as well as bystanders that might interact with the animal indirectly (e.g., by being near enough to affect the animal via pheromones or emanated electromagnetic fields). By blocking or attenuating electromagnetic fields emanating from a person near the animal, the animal is less likely to sense such fields that arise from an emotional response or state of the person, and is therefore also less likely to react to that emotional state or reaction. In particular, emotional responses or states that might cause undesirable behavior of the animal (e.g., flight or aggression) are less likely to be sensed by the animal. Such emotional states or responses can arise for a variety of reasons, e.g., a handler's or bystander's fear of the animal, a handler's frustration with the animal's behavior or response (or lack thereof) to its training, a handler's frustration or discomfort while being taught how to handle an animal, or an instructor's frustration at a handler trainee's response (or lack thereof) to his/her instruction.

Figure 5A:
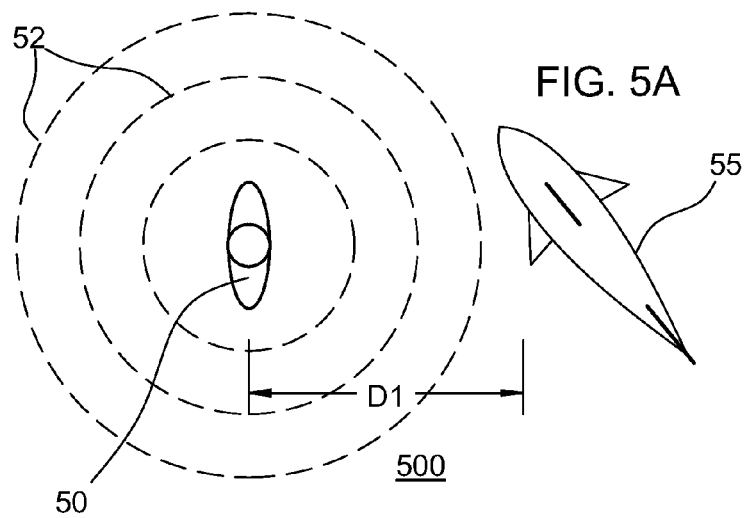
FIGS. 5A and 5B are schematic top views illustrating the approach of a water-borne predator toward a person in a body of water with and without, respectively, electromagnetically shielding apparel.
Figure 5B:
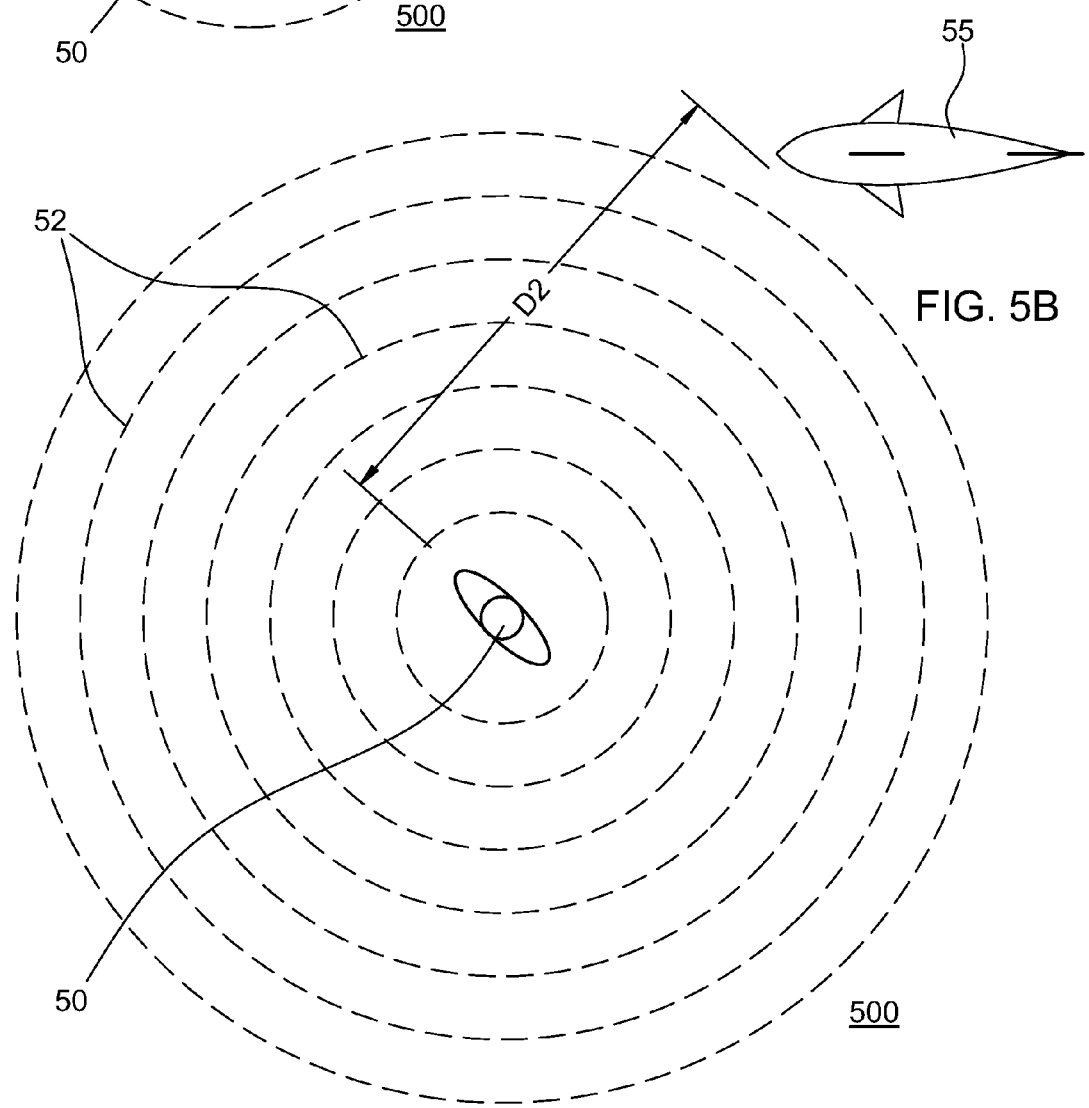

In another example, electromagnetic shielding can be incorporated into any suitable apparel worn while the wearer 50 is in or on a body of water 500 (e.g., river, lake, sea, ocean), as in FIGS. 5A-5B. Blocking or attenuating the electromagnetic field 52 emanated at frequencies less than about 1 gigahertz by the person 50 can reduce the likelihood of detection of the wearer 50 by an aquatic or marine water-borne predator 55, e.g., a shark. Without electromagnetically shielding apparel (as in FIG. 5B), the predator 55 might detect the person in the water from a larger distance D2. With electromagnetically shielding apparel (as in FIG. 5A), the predator 55 might only detect the person 50 in the water after approaching more closely (distance D1 that is smaller than distance D2). Shielding of a person's emanated electromagnetic field while in a body of water can be particularly advantageous under conditions of poor underwater visibility, wherein a water-borne predator might rely more heavily on electromagnetic prey detection, and wherein a person would have more difficulty seeing or avoiding a water-borne predator. Electromagnetically shielding apparel can be provided to or worn by, e.g., bathers, waders, swimmers, surfers, boaters, sailors, personal water craft users, wind surfers, para-sailors, para-surfers, snorkelers, or divers (free, scuba, or other) in a river, lake, sea, ocean, or other body of water. Examples of suitable articles of apparel can include, but are not limited to, trunks, shirts, bathing suits, wet suits, dry suits, deck apparel, and so on. Some examples are shown in FIG. 2. Electromagnetically shielding apparel can be included with other water survival gear on a vessel or aircraft, or electromagnetically shielding fabric can be incorporated into conventional survival gear, e.g., a life vest, life raft, or exposure suit. There is no teaching or suggestion in the prior art to attenuate or block electromagnetic fields emanating from a person in or on a body of water, or that such attenuation or blocking would be desirable.

The electromagnetically shielding fabric can block or attenuate electric fields, magnetic fields, or both, and any of those alternatives shall fall within the scope of the present disclosure or appended claims. It may be preferable under particular circumstances to preferentially block either electric fields or magnetic fields, and such uses are encompassed by the present disclosure or appended claims.

Figure 4A:
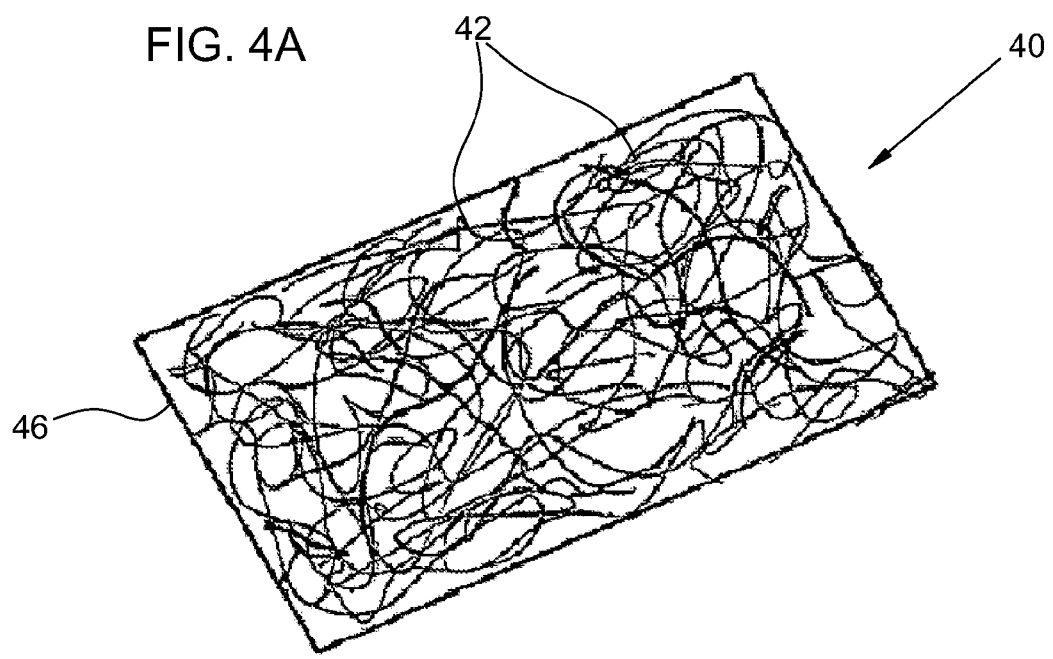
FIGS. 4A and 4B illustrate exemplary electromagnetically shielding fabrics.
Figure 4B:
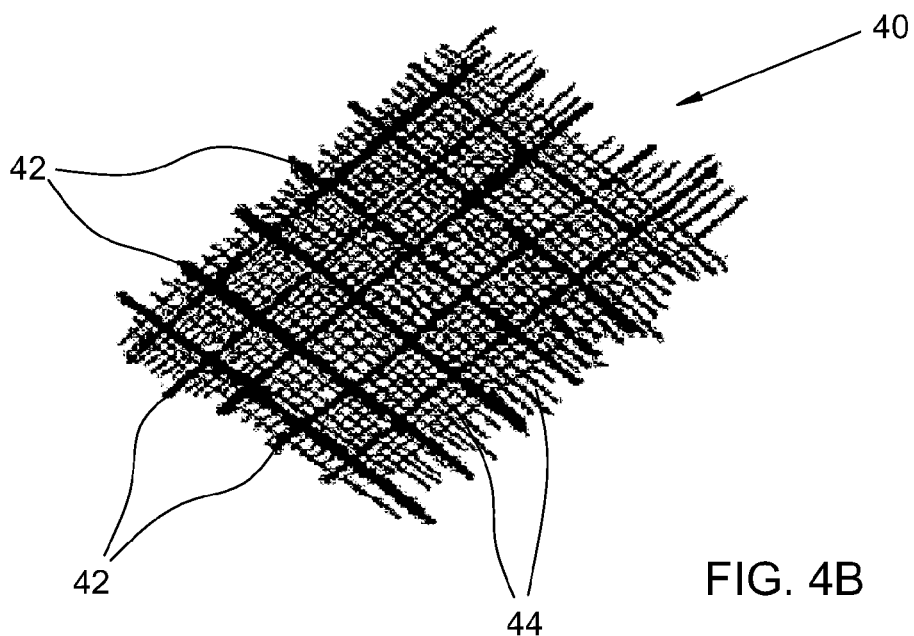

Any suitable fabric can be employed that incorporates conductive fibers of any suitable type to form a substantially continuous electrical conduction network in the fabric. The conduction network 42 can be arranged irregularly (as in the example of FIG. 4A), in a grid-like pattern (as in the example of FIG. 4B), or in any other suitable, desirable, or practicable arrangement. The conductive fibers can be intermingled with non-conductive fibers 44 to form the shielding fabric 40 (in a regular, interwoven arrangement or in an irregular arrangement). Examples of suitable fibers include typical textile fibers, e.g., wool, silk, or other natural polyamide fibers; cotton, rayon, or other cellulosic fibers; or nylon, polyester, Kevlar, or other synthetic fibers. Alternatively, the conductive fibers 42 (regularly or irregularly arranged) can be applied to a surface of a non-conducting fabric 46 to form the shielding fabric 40. In that latter case, the non-conducting fabric can comprise a woven, textile fabric, or can comprise a substantially continuous sheet fabric such as a plastic sheet or polymer film. The conductive fibers can be combined with the non-conducting fabric in any suitable, desirable, or practicable way, including those described above or others not explicitly disclosed herein, and all such combinations shall fall within the scope of the present disclosure or appended claims.

Any suitable conductive fibers can be employed that provide sufficient conductivity for providing electromagnetic shielding and that can form fibers suitable for incorporation into a fabric. In various examples disclosed in the incorporated references, the conductive fibers comprise stainless steel, copper, silver, carbon fibers or nanotubes, conductive ceramic, conductive polymer, or conductive nanotubes. Any suitable composition of the electromagnetic shielding fabric can be employed. One suitable example is Farabloc® fabric described in incorporated U.S. Pat. Nos. 4,653,473, 4,825,877, 6,146,351, and 6,868,854. In various examples of such fabrics disclosed in the incorporated references, the fabric includes between about 2% and about 35% by weight of the conductive fibers. Other exemplary fabrics can include greater than about 5%, greater than about 10%, greater than about 15%, greater than about 20%, greater than about 25%, or greater than about 30% by weight of the conductive fibers, while still other exemplary fabrics can include less than about 30%, less than about 25%, less than about 20%, less than about 15%, less than about 10%, or less than about 5% by weight of the conductive fibers. Fabrics having greater than 35% by weight of conductive fibers can be employed if suitable, desirable, or practicable. Higher compositions of conductive fiber typically can provide greater electromagnetic shielding, but might also come at a higher cost or weight, or might yield a fabric with other undesirable properties. Any suitably optimized composition can be used in a given situation.

In addition to providing electromagnetic shielding, the article of apparel can also be adapted or arranged to decrease visual or olfactory perception of the wearer by an animal or another person. For example, camouflage clothing, hoods or other headwear, glasses or other eyewear, or hunting blinds are conventionally used to conceal a hunter or wildlife observer from hunted or observed animals. Such visual camouflage causes the hunter to blend in with the surroundings, making him or her less visible to a prey animal. In addition to visual camouflage, hunting apparel or a hunting blind can also include an odor or scent absorber, suppressant, attenuator, or blocker, for attenuating scent or odor arising from the wearer (e.g., sweat, pheromones, or body odor) or from microbial growth in the apparel. Examples of various hunting apparel and hunting blinds incorporating camouflage or odor suppression can be found in the following references, each of which is incorporated by reference as if fully set forth herein:

Pat. Pub No. 2007/0226868 entitled "Low-cost disposable odor-reducing hunting clothing" published Oct. 4, 2007 in the name of Hunt;

U.S. Pat. No. 7,182,091 entitled "Hunting blind and method of use thereof" issued Feb. 27, 2007 to Maddox;

Pat. Pub No. 2006/0147698 entitled "Garments preventing transmission of human body odor" published Jul. 6, 2006 in the names of Carroll et al; and Pat. Pub. No. 2004/0209051 entitled "Camouflage U.S. Marine Corps utility uniform: pattern, fabric, and design" published Oct. 21, 2004 in the names of Santos et al;

Pat. Pub No. 2004/0107474 entitled "Odor absorbing article of clothing" published Jun. 10, 2004 in the name of Sesselmann.

U.S. Pat. No. 6,694,995 entitled "Rapidly-opening hunting blind" issued Feb. 24, 2004 to Ransom;

U.S. Pat. No. 6,632,499 entitled "Hunter camouflage system" issued Oct. 14, 2003 to Marks et al;

U.S. Pat. No. 6,539,966 entitled "Removable cover for a hunting blind" issued Apr. 1, 2003 to Raines et al;

Pat. Pub No. 2002/0069449 entitled "Hood including three-dimensional covering" published Jun. 13, 2002 in the names of Blutstein et al;

U.S. Pat. No. 6,061,828 entitled "Camouflage items and camouflage material thereon" issued May 16, 2000 to Josephs;

U.S. Pat. No. 5,767,933 entitled "Camouflage eyewear" issued Jun. 16, 1998 to Hagan;

U.S. Pat. No. 5,675,838 entitled "Camouflage clothing" issued Oct. 14, 1997 to Hollinger;

U.S. Pat. No. 5,521,655 entitled "Camouflage eyewear" issued May 28, 1996 to Rhoad;

U.S. Pat. No. Des. 350,399 entitled "Hunting blind" issued Sep. 6, 1994 to Bodrie;

U.S. Pat. No. Des. 337,366 entitled "Hunting blind" issued Jul. 13, 1993 to Baker; and U.S. Pat. No. 5,203,033 entitled "Camouflaged garment" issued Apr. 20, 1993 to Sheppard et al.

Visual camouflage and/or scent/odor reduction can serve to reduce the ability of an animal (predator or prey) or another person to perceive the presence of the wearer, by sight or scent, respectively, and can be incorporated into electromagnetically shielding apparel. Scent/odor reduction, in combination with electromagnetic shielding, can also advantageously (i) reduce the effect on an animal of the emotional state or emotional response of the wearer, (ii) reduce the likelihood of detection of the wearer by an aquatic or marine water-borne predator, or (iii) reduce any alerting or cueing of a human adversary arising from an emotional state or an emotional response of the wearer.

Figure 3A:
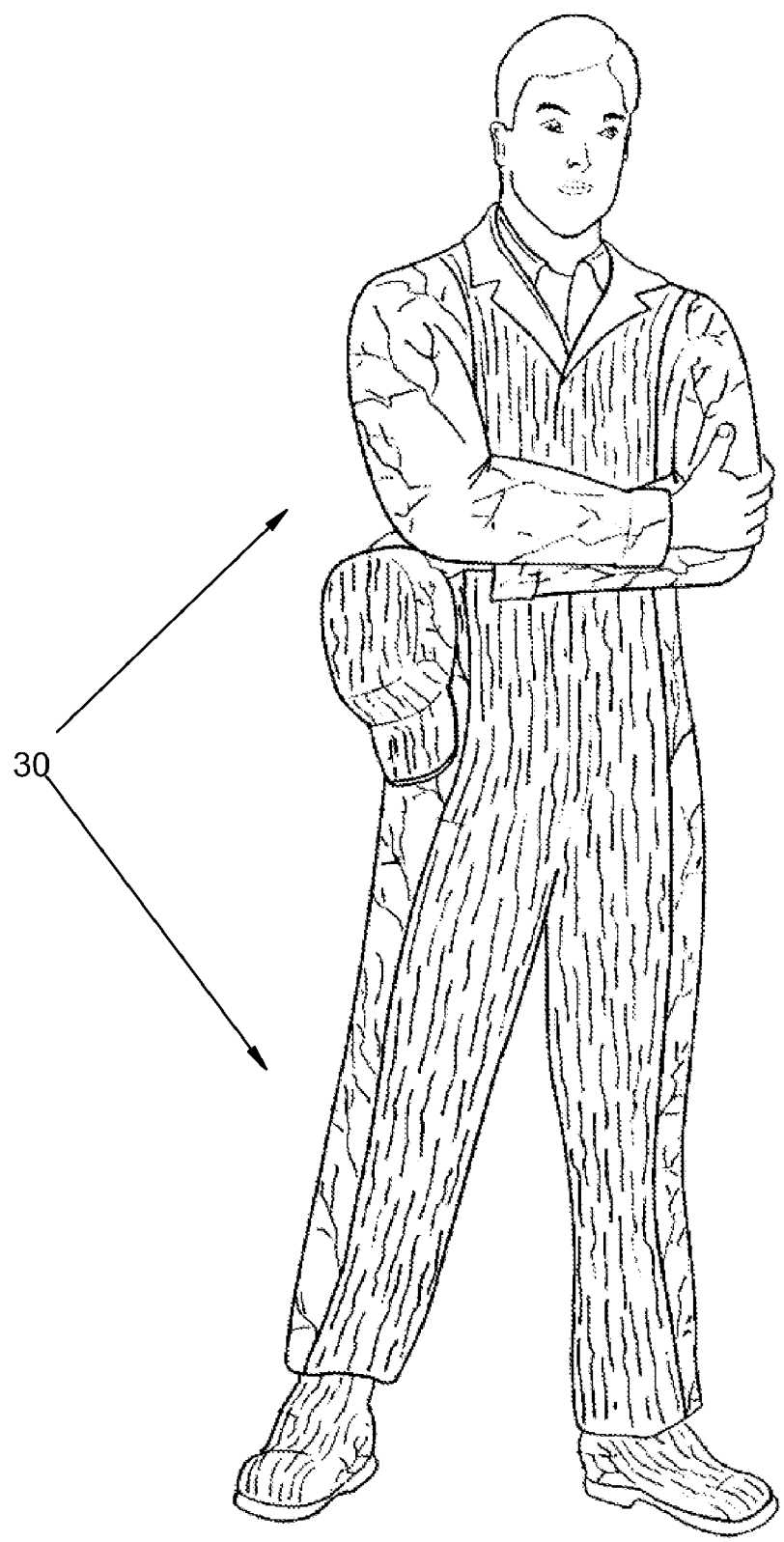
FIGS. 3A and 3B illustrate exemplary articles of electromagnetically shielding apparel that include exemplary visual camouflage patterns.
Figure 3B:
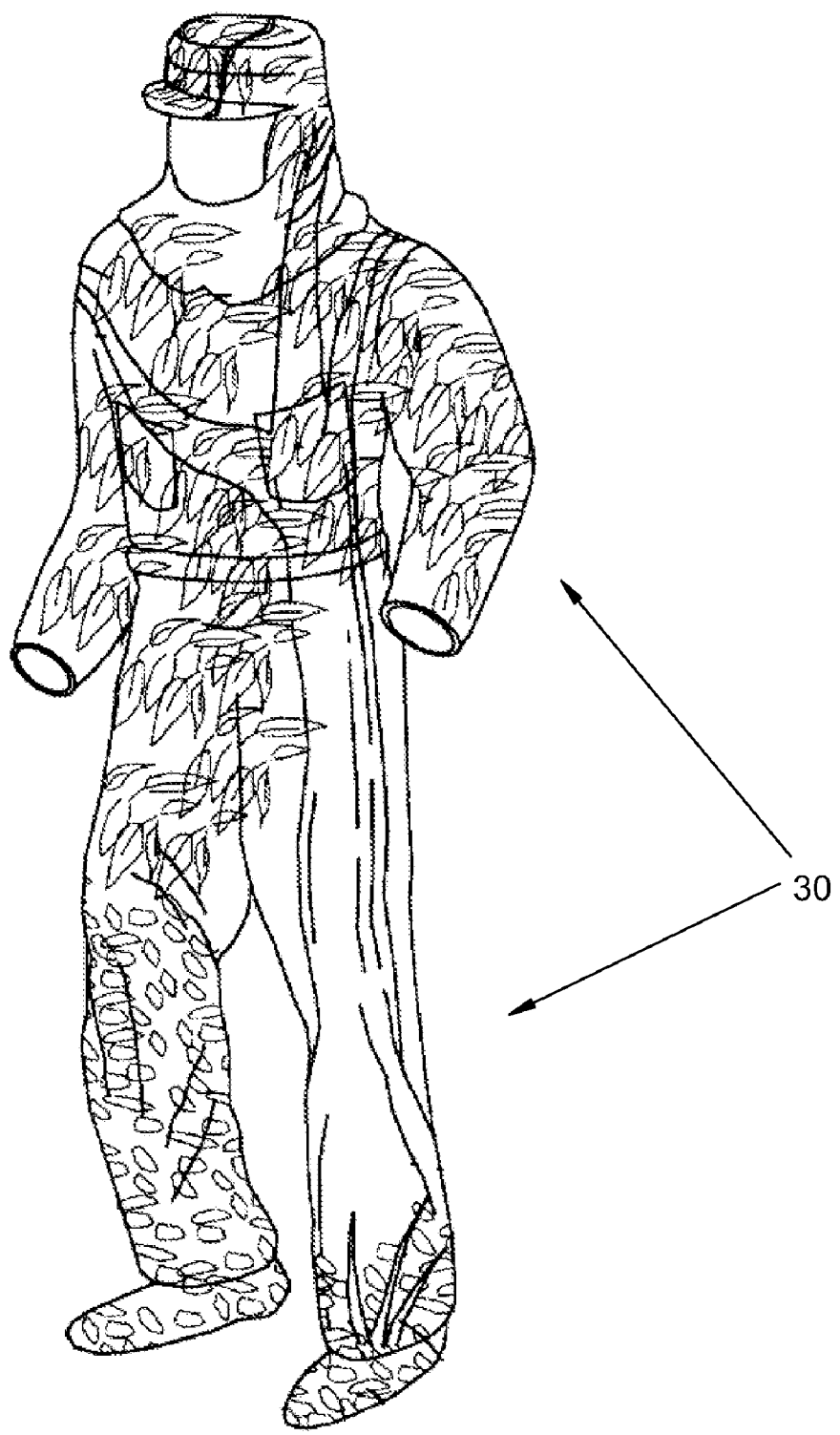

Exemplary articles of electromagnetically shielding apparel 30 can include a visual camouflage pattern on at least a portion of its outer surface (as in FIGS. 3A and 3B). Many examples of such visual camouflage are known, and some examples are disclosed in various of the incorporated references. Any suitable visual camouflage pattern, including both two- and three-dimensional patterns, shall fall within the scope of the present disclosure or claims. In another example, the article of electromagnetically shielding apparel can include an odor or scent absorber, suppressant, attenuator, or blocker. Some examples of these are disclosed in various of the incorporated references. Any suitable scent/odor absorber, suppressant, attenuator, or blocker shall fall within the scope of the present disclosure or claims, including those that act by absorbing or masking the scent/odor or by inhibiting microbial growth. By combining electromagnetic shielding with visual camouflage and/or scent/odor control, the overall likelihood that the user's emanated electromagnetic field or emanated scent/odor will affecting progress or an outcome of a given situation (including those disclosed herein) can be reduced.

Conductive fibers can be employed that also attenuate a scent or odor emanating from the wearer of the apparel. Conductive fibers can be employed that attenuate the scent or odor by at least partly absorbing or masking it or by inhibiting microbial growth in the apparel. Attenuating scent or odor emanating from the wearer decreases the likelihood of such emanated scent or odor affecting progress or the outcome of the given situation in which the wearer is involved (including those variously described herein). Apparel disclosed herein that attenuates both electromagnetic fields and scent or odor emanating from a wearer can be generally referred to as "attenuating apparel," and that phrase shall be understood to encompass apparel constructed from fabric that incorporates conductive fibers that also attenuate scent or odor.

To provide apparel that attenuates a wearer's emanated scent or odor in addition to attenuating the wearer's emanated electromagnetic field, conducting fibers can be employed that provide both of those functions. In one example, copper or silver conductive fibers can be employed to attenuate emanated electromagnetic fields (due to their conductivity) and to attenuate emanated scent or odor (due to their observed antimicrobial properties). Silver or copper conductive fibers can be incorporated in to the apparel in any suitable fabric type at any suitable composition. In another example, conductive carbon fibers can be employed to attenuate both emanated electromagnetic fields and emanated scent or odor. It has been observed that conductive carbon fibers incorporated into a shielding fabric appear to absorb at least a portion of emanated scent or odor. Multifilament carbon fiber yarn has been observed to attenuate scent or odor more effectively than monofilament yarn. An exemplary fabric for constructing apparel can comprise a 20 denier, three filament carbon fiber yarn twisted with 50 denier polyester yarn and knitted or woven into a textile fabric. Any suitable yarn type or density can be employed.

In addition to the situations already described (animal handling, in or on a body of water, or an adversarial situation), attenuating apparel can be advantageously employed to attenuate, while hunting, the electromagnetic field emanated at frequencies less than about 1 gigahertz by a hunter and a scent or odor emanated by the hunter. Hereafter the term "hunter" shall include a hunter or an observer of wildlife (unless the particular context makes it clear that that equivalence would not apply), and "hunting" shall include hunting or observing (such as by photographing, filming, recording, or merely viewing or listening to the animal). The electromagnetic field and scent/odor can be attenuated by one or more articles of apparel worn by the hunter while hunting.

Another exemplary method comprises attenuating, while hunting, the electromagnetic field and scent/odor emanated by a hunter, using attenuating apparel incorporating conductive fibers that also attenuate scent/odor. Another exemplary method can include providing at least one such article of attenuating apparel to a hunter and instructing that hunter to wear the article while hunting. That method can also include constructing at least one said article of apparel prior to providing it to the hunter.

Figure 1B:
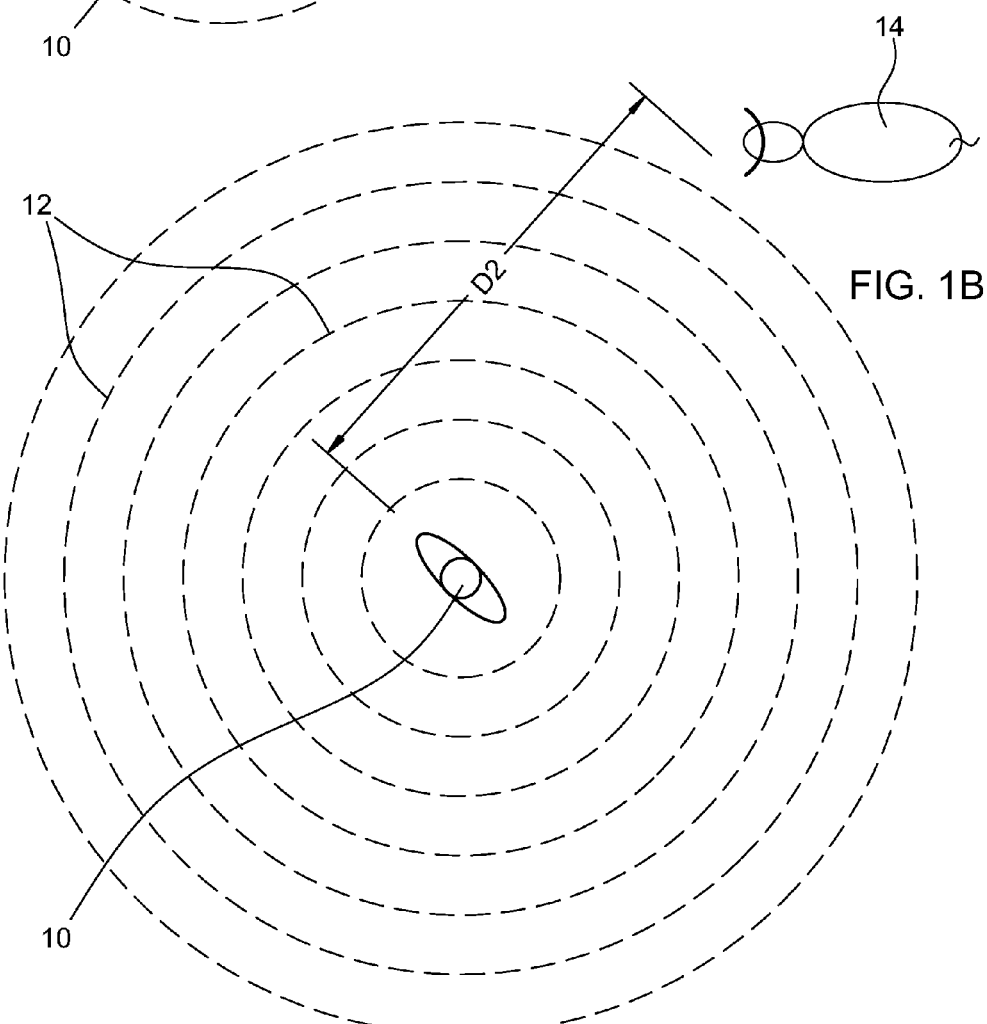

The hunter wears the article of attenuating apparel while hunting. The attenuating fabric blocks or attenuates an electromagnetic field and a scent/odor emanating from the hunter, thereby decreasing the likelihood that he or she will be detected by an animal sensitive to such electromagnetic fields or scents/odors. An electromagnetic field 12 emanated by a hunter 10 and thus attenuated can be detected by an animal 14 at a maximum distance D1 (FIG. 1A) that is smaller than the maximum detection distance D2 at which an unattenuated field 12 (FIG. 1B) can be detected by that same animal 14. Detection of the scent/odor by the animal can be similarly described. The hunter 10 can therefore approach the animal 14 more closely without detection, facilitating the kill or observation. In measurements of electromagnetic fields emanating from a human body, reductions of field strength ranging from about 38% to about 65% have been observed, as illustrated in the case studies and the Appendix attached to several of the applications incorporated above. Any suitable, desirable, or practicable reduction of emanated electromagnetic field strength shall fall within the scope of the present disclosure or appended claims.

The article of attenuating apparel comprises an attenuating fabric incorporating conductive fibers that also attenuate of block the hunter's scent or odor. Such attenuation of emanated electromagnetic field and scent/odor can enable the hunter to approach more closely (without detection) an animal in its habitat, thereby increasing the likelihood of a successful kill or observation. Fabric incorporating fibers that attenuate both electromagnetic fields and scent/odor can also (or instead) be employed in a hunting blind, in which a hunter or observer can remain stationary and wait for an animal to approach his/her position.

It is possible in some instances of hunting that a human hunter might become the prey of a predatory animal, either the animal he is hunting or another animal in the same habitat. In those circumstances, the attenuating apparel can reduce the likelihood that the predatory animal will locate the human hunter by detecting the electromagnetic field or scent/odor emanated by the hunter.

There is no teaching or suggestion in the prior art to attenuate or block (using such fabrics) electromagnetic fields and scent/odor emanating from a hunter while hunting or an observer while observing wildlife, or that attenuation or blocking using such fabrics would be desirable. There is no teaching or suggestion in the prior art to incorporate attenuating fabric (incorporating conductive fibers that also attenuate scent/odor) into hunting apparel or a hunting blind, or that the incorporation of such fabrics would be desirable.

Any other use of electromagnetically shielding clothing (with or without odor/scent attenuation), in a situation wherein blocking or attenuating the wearer's emanated electromagnetic field may be advantageous, shall fall within the scope of the present disclosure, whether that situation involves an animal or not.

It is intended that equivalents of the disclosed exemplary embodiments and methods shall fall within the scope of the present disclosure or appended claims. It is intended that the disclosed exemplary embodiments and methods, and equivalents thereof, may be modified while remaining within the scope of the present disclosure or appended claims.

In the foregoing Detailed Description, various features may be grouped together in several exemplary embodiments for the purpose of streamlining the disclosure. This method of disclosure is not to be interpreted as reflecting an intention that any claimed embodiment requires more features than are expressly recited in the corresponding claim. Rather, as the appended claims reflect, inventive subject matter may lie in less than all features of a single disclosed exemplary embodiment. Thus, the appended claims are hereby incorporated into the Detailed Description, with each claim standing on its own as a separate disclosed embodiment. However, the present disclosure shall also be construed as implicitly disclosing any embodiment having any suitable set of one or more disclosed or claimed features (i.e., sets of features that are not incompatible or mutually exclusive) that appear in the present disclosure (including incorporated applications) or the appended claims, including those sets that may not be explicitly disclosed herein. It should be further noted that the scope of the appended claims do not necessarily encompass the whole of the subject matter disclosed herein.

For purposes of the present disclosure and appended claims, the conjunction "or" is to be construed inclusively (e.g., "a dog or a cat" would be interpreted as "a dog, or a cat, or both"; e.g., "a dog, a cat, or a mouse" would be interpreted as "a dog, or a cat, or a mouse, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure or appended claims, the words "comprising," "including," "having," and variants thereof, wherever they appear, shall be construed as open ended terminology, with the same meaning as if the phrase "at least" were appended after each instance thereof.

In the appended claims, if the provisions of 35 USC §112 ¶6 are desired to be invoked in an apparatus claim, then the word "means" will appear in that apparatus claim. If those provisions are desired to be invoked in a method claim, the words "a step for" will appear in that method claim. Conversely, if the words "means" or "a step for" do not appear in a claim, then the provisions of 35 USC §112 ¶6 are not intended to be invoked for that claim.

The Abstract is provided as required as an aid to those searching for specific subject matter within the patent literature. However, the Abstract is not intended to imply that any elements, features, or limitations recited therein are necessarily encompassed by any particular claim. The scope of subject matter encompassed by each claim shall be determined by the recitation of only that claim.

What is claimed is:

1. A method comprising attenuating, while involved in a human adversarial situation, one's own emanated electromagnetic field at frequencies less than about 1 gigahertz by wearing one or more articles of apparel that include an electromagnetically shielding fabric, which shielding fabric comprises a substantially continuous system of conductive fibers combined with a non-conductive fabric and attenuates the emanated electromagnetic field at frequencies less than about 1 gigahertz, wherein said attenuating one's own emanated electromagnetic field at frequencies less than about 1 gigahertz decreases the likelihood of one's own emanated electromagnetic field alerting or cueing a human adversary and thereby decreases the likelihood of that emanated electromagnetic field affecting progress or an outcome of the human adversarial situation.

2. The method of claim 1 wherein the electromagnetically shielding fabric attenuates the emanated electromagnetic field at frequencies less than about 1 megahertz, and said attenuating of one's own emanated electromagnetic field at frequencies less than about 1 megahertz decreases the likelihood of one's own emanated electromagnetic field alerting or cueing a human adversary and thereby decreases the likelihood of that emanated electromagnetic field affecting the progress or the outcome of the human adversarial situation.

3. The method of claim 2 wherein the electromagnetically shielding fabric attenuates the emanated electromagnetic field at frequencies less than about 1 kilohertz, and said attenuating of one's own emanated electromagnetic field at frequencies less than about 1 kilohertz decreases the likelihood of one's own emanated electromagnetic field alerting or cueing a human adversary and thereby decreases the likelihood of that emanated electromagnetic field affecting the progress or the outcome of the human adversarial situation.

4. The method of claim 1 wherein the conductive fibers are intermingled with non-conductive fibers that form the non-conducting fabric.

5. The method of claim 1 wherein the conductive fibers are applied to a surface of the non-conducting fabric.

6. The method of claim 1 wherein at least one of the articles of apparel comprises an article of clothing, footwear, headwear, or eyewear.

7. The method of claim 1 wherein the shielding fabric includes between about 2% and about 35% by weight of the conductive fibers.

8. The method of claim 1 wherein the conductive fibers comprise stainless steel, copper, silver, conductive ceramic, carbon fiber or nanotubes, carbon monofilament or multifilament yarn, conductive polymer, or conductive nanotubes.

9. The method of claim 1 wherein at least one of the articles of apparel includes an odor absorber, suppressant, attenuator, or blocker.

10. The method of claim 9 wherein the conductive fibers act as the odor absorber, suppressant, attenuator, or blocker.

11. The method of claim 10 wherein the conductive fibers at least partly absorb the scent or odor and comprise carbon fibers, carbon monofilament yarn, or carbon multifilament yarn.

12. The method of claim 1 wherein the human adversarial situation includes one or more of: (i) a team or individual athletic contest; (ii) a mental or verbal contest; (iii) board or card games; (iv) an interview, debriefing, or interrogation; (v) a law enforcement situation; (vi) a military, combat, or tactical situation; or (vii) a covert operation.

13. A method comprising:
providing to a user one or more articles of apparel that include an electromagnetically shielding fabric, which shielding fabric comprises a substantially continuous system of conductive fibers combined with a non-conductive fabric and attenuates the user's emanated electromagnetic field at frequencies less than about 1 gigahertz; and
instructing the user to wear, while involved in a human adversarial situation, at least one of the articles of apparel,
wherein said attenuating of the user's emanated electromagnetic field at frequencies less than about 1 gigahertz decreases the likelihood of the user's emanated electromagnetic field alerting or cueing a human adversary and thereby decreases the likelihood of that emanated electromagnetic field affecting progress or an outcome of the human adversarial situation.

14. The method of claim 13 wherein the electromagnetically shielding fabric attenuates the emanated electromagnetic field at frequencies less than about 1 megahertz, and said attenuating of the user's emanated electromagnetic field at frequencies less than about 1 megahertz decreases the likelihood of the user's emanated electromagnetic field alerting or cueing a human adversary and thereby decreases the likelihood of that emanated electromagnetic field affecting progress or an outcome of the human adversarial situation.

15. The method of claim 14 wherein the electromagnetically shielding fabric attenuates the emanated electromagnetic field at frequencies less than about 1 kilohertz, and said attenuating of the user's emanated electromagnetic field at frequencies less than about 1 kilohertz decreases the likelihood of the user's emanated electromagnetic field alerting or cueing a human adversary and thereby decreases the likelihood of that emanated electromagnetic field affecting progress or an outcome of the human adversarial situation.

16. The method of claim 13 further comprising constructing at least one of the articles of apparel prior to providing it to the user.

17. The method of claim 13 wherein the conductive fibers are intermingled with non-conductive fibers that form the non-conducting fabric.

18. The method of claim 13 wherein the conductive fibers are applied to a surface of the non-conducting fabric.

19. The method of claim 13 wherein at least one of the articles of apparel comprises an article of clothing, footwear, headwear, or eyewear.

20. The method of claim 13 wherein the shielding fabric includes between about 2% and about 35% by weight of the conductive fibers.

21. The method of claim 13 wherein the conductive fibers comprise stainless steel, copper, silver, conductive ceramic, carbon fiber or nanotubes, carbon monofilament or multifilament yarn, conductive polymer, or conductive nanotubes.

22. The method of claim 13 wherein at least one of the articles of apparel includes an odor absorber, suppressant, attenuator, or blocker.

23. The method of claim 22 wherein the conductive fibers act as the odor absorber, suppressant, attenuator, or blocker.

24. The method of claim 23 wherein the conductive fibers at least partly absorb the scent or odor and comprise carbon fibers, carbon monofilament yarn, or carbon multifilament yarn.

25. The method of claim 13 wherein the human adversarial situation includes one or more of: (i) a team or individual athletic contest; (ii) a mental or verbal contest; (iii) board or card games; (iv) an interview, debriefing, or interrogation; (v) a law enforcement situation; (vi) a military, combat, or tactical situation; or (vii) a covert operation.

* * * * *